United States Patent [19]
Wiley et al.

[11] Patent Number: 4,887,593
[45] Date of Patent: Dec. 19, 1989

[54] METHOD AND APPARATUS FOR ELECTROSURGICALLY RESECTIONING AN EQUINE SOFT PALATE TO ALLEVIATE OCCLUSION OF THE BREATHING PASSAGEWAY

[76] Inventors: Michael J. Wiley, 4721 Tanglewood Ct., Norman, Okla. 73072; Helen J. Albrecht, 14500 S. Pennsylvania,. Oklahoma City, Okla. 73170; Albie A. Dale, 300 36th Ave., S.W., Norman, Okla. 73072

[21] Appl. No.: 302,001

[22] Filed: Jan. 26, 1989

[51] Int. Cl.$^4$ ............................................... A61B 17/36
[52] U.S. Cl. ..................................... 606/45; 219/227; 606/49
[58] Field of Search ... 128/305, 303.1, 303.11–303.17, 128/898; 30/116, 117, 140; 219/227, 229, 233, 234, 221

[56] References Cited

U.S. PATENT DOCUMENTS

| | | | |
|---|---|---|---|
| 712,989 | 11/1902 | Washburn | 128/303.1 |
| 1,919,543 | 7/1933 | Doane | |
| 2,002,559 | 5/1935 | Wappler | |
| 2,447,169 | 1/1945 | Sousa | 128/303.14 |
| 3,089,496 | 5/1963 | Degelman | |
| 3,636,943 | 1/1972 | Balamuth | |
| 3,801,766 | 4/1974 | Morrison, Jr. | |
| 3,915,169 | 10/1975 | McGuire | 128/305 |
| 4,273,127 | 6/1981 | Auth et al. | |
| 4,318,409 | 3/1982 | Oosten | |
| 4,427,006 | 1/1984 | Nottke | |
| 4,506,668 | 3/1985 | Konig | |
| 4,512,343 | 4/1985 | Falk et al. | |
| 4,531,524 | 7/1985 | Mioduski | 128/303.15 |
| 4,534,347 | 8/1985 | Taylor | |
| 4,545,375 | 10/1985 | Cline | 128/303.17 |

Primary Examiner—Michael H. Thaler
Assistant Examiner—William Lewis
Attorney, Agent, or Firm—Laney, Dougherty, Hessin & Beavers

[57] ABSTRACT

A method and apparatus for electrosurgically resectioning the soft palate of a horse includes an elongated, semi-rigid, yet forceably flexible, shaft which carries an electrical conductor over its length. The shaft has a bight at one end across which the conductor is extended as a thin wire in an exposed, cutting position. At its other end the shaft is connected to a pistol-grip switch handle. A three-position toggle switch is mounted in the handle and connected to the conductor. The toggle switch can be placed in either a coagulating or cutting mode position.

In practicing the method using the described apparatus, the bight-carrying end of the shaft is inserted in one of the nasal passageways of a horse suffering from a reduction in breathing inhalation capacity as a result of a partial occlusion of the windpipe by unnatural displacement of the soft palate. An illuminating endoscope is inserted in the other nasal passageway. Both shaft and endoscope are advanced into the respective nasal passageways until the endoscope shows the bight to be positioned over the displaced soft palate. The handle is then manipulated to bring the wire section of the conductor crossing the bight into contact with the center of the soft palate. The instrument is then placed in a cutting status by proper manipulation of the toggle switch. The palate is cut through in a resectioning step, followed by a coagulating step effected by shifting of the toggle switch.

14 Claims, 1 Drawing Sheet

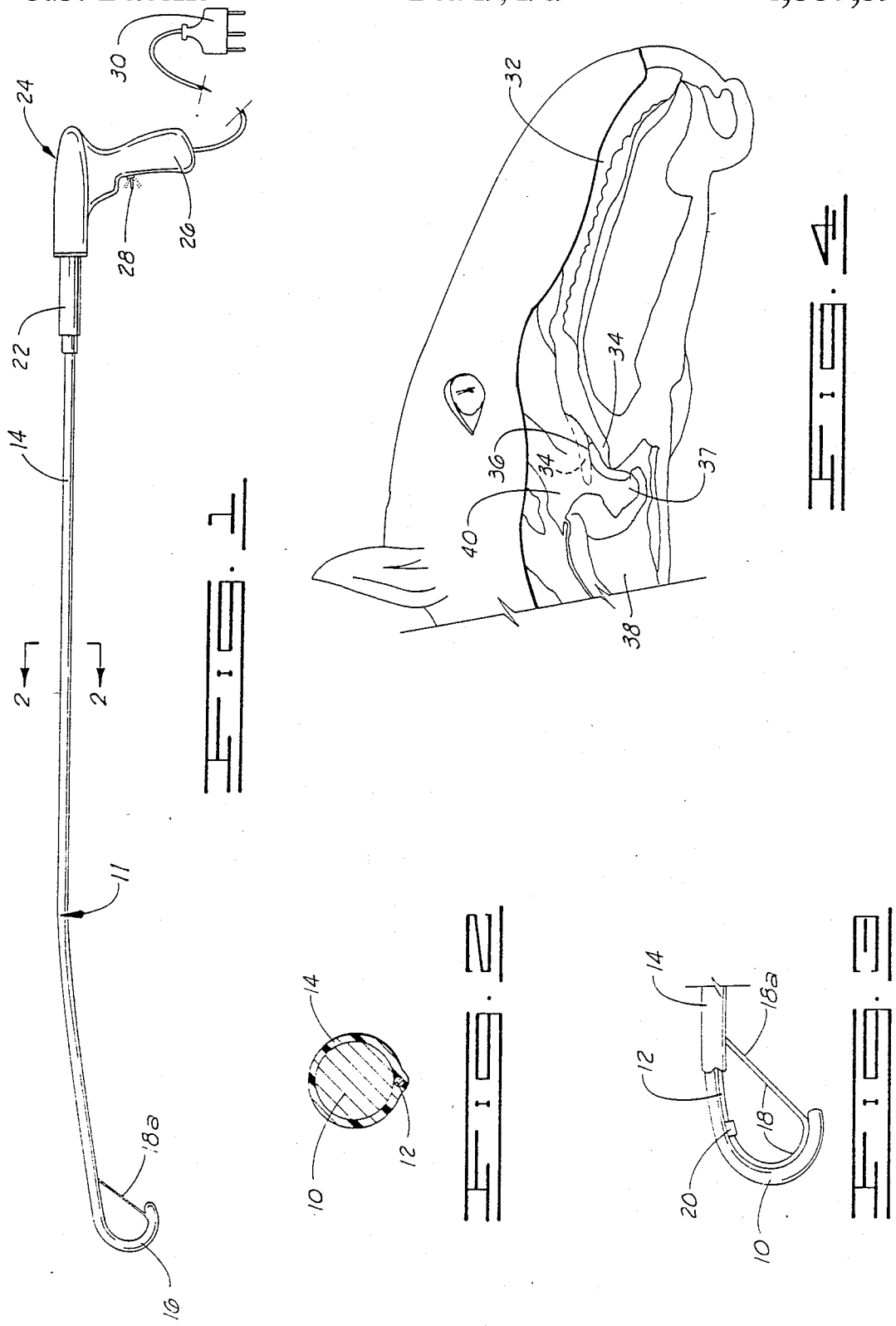

METHOD AND APPARATUS FOR ELECTROSURGICALLY RESECTIONING AN EQUINE SOFT PALATE TO ALLEVIATE OCCLUSION OF THE BREATHING PASSAGEWAY

FIELD OF THE INVENTION

This invention relates to a method and an apparatus for relieving impaired breathing capacity of a equine animal resulting from the displacement of the soft palate to a position immediately overlying the epiglottis. The apparatus used is an electrosurgical instrument for resectioning the palate, which instrument is uniquely shaped to afford the capability of reaching and effectively severing or cleaving the palate by high intensity electrical current, followed by coagulation of the surgical cut to reduce hemorrhaging therefrom.

BACKGROUND OF THE INVENTION

BRIEF DESCRIPTION OF THE PRIOR ART

It is known in surgery to use certain types of electrical devices for resectioning organs of the human body in a way such that the resectioning procedure is virtually hemostatic in character, or to use a cauterizing or coagulating-type current application following a procedure involving surgical cutting, so as to thereby reduce the risk of excessive trauma or injury from hemorrhaging to a minimum.

Patents which have described systems of this type include Falk et al U.S. Pat. No. 4,512,343 which discloses a medical coagulating instrument. This instrument includes an elongated conductive shaft with an insulating jacket. At one end, an insulating handle is provided for manipulation by the surgeon during use. The electrically conductive shaft is insulated by means of a jacket of insulating material which is sleeved onto the shaft. A connector is provided at the proximal end of the shaft to facilitate connection to a high frequency current source.

The insulating sleeve placed on the shaft can desirably include a plurality of individual plastic conduit pieces which are individually injected molded and dimensioned to slip over the shaft with a close fit providing abutting end faces which engage each other to form a substantially continuous sleeve. A second insulating sleeve can be placed over that which is next to the shaft by providing a heat-shrink plastic material on the outer side of the initial sleeve.

Taylor U.S. Pat. No. 4,534,347 discloses a microwave coagulating scalpel which simultaneously cuts and coagulates. The instrument is particularly useful for resectioning highly vascular tissue. The scalpel blade forms both a cutting edge and a microwave radiator loop. Organs which can be especially usefully resectioned and coagulated with the instrument described in this patent are the spleen and the liver. In the use of the instrument, the microwave-induced thermal field creates a coagulated crust which rapidly heals following the surgical resectioning. This patentee acknowledges that other types of electrosurgical techniques have been employed using resistance-heated scalpels, radio frequency cutting devices of both the unipolar and bipolar-type and plasma scalpels.

The first commercial radio frequency scalpels appeared in 1926 but were not generally accepted by surgeons until the development of non-explosive anesthetics in the late 1950's. Later, in the 1970's, solid state R.F. scalpels were developed and have been widely installed in operating rooms. Cutting and coagulation occur at the tip of a probe electrode where the current is concentrated. After passing through the zone of the flesh to be cut, the current then dissipates and spreads out through the body of the patient to a large "butt plate" upon which the patient rests. Whether the instrument cuts or coagulates is determined by the electrical power and wave form applied to the conductor. Examples of scalpels of this type are disclosed in U.S. Pat. Nos. 3,089,496 and 4,318,409.

In conventional electrosurgery, the cutting of tissue is achieved by an electric current discharge. The region of intense current is of a short path, but heats the tissue intensely, causing the cells to actually burst into steam. The cutting thus occurring is caused by the discharge of an appropriate electrode to the tissue. The sharpened blade forming the electrode does not actually effect mechanical cutting. Desiccation, cauterization or coagulation in conventional electrosurgery are caused by holding the active electrode in polar contact with the tissue. The electric current passes directly into the tissue, thereby causing localized resistance heating because this resistance heating occurs primarily at the zone of contact between the active electrode and the tissue. The cauterization or coagulation effect is very shallow, and in some instances is thought to be too shallow to be used effectively to cauterize or desiccate highly vascular tissues of large areas, such as spleens and livers.

Where microwave energy is used in the instrument for simultaneous severing and surgically coagulating, the patient need not be grounded through a "butt plate", or other arrangement, as is normally utilized and required in conventional radio frequency scalpel techniques.

U.S. Pat. No. 4,273,127 discloses the use of a laser for cutting and coagulating tissue. A carbon dioxide laser scalpel is used to produce the coagulation, but blood loss is still excessive in incisions which involve large areas of highly vascularized tissue.

U.S. Pat. No. 3,636,943 discloses a method and apparatus for using ultrasonic energy to close off small, severed blood vessels during surgery. The ultrasonic device produces heat by means of mechanical friction to achieve the cauterization.

In U.S. Pat. No. 4,534,347 discussed above, the surgical blade which is used for resectioning is shaped to form a microwave radiating loop extending between an inner conductor and an outer or external conductor of a rigid coaxial conductor 10. The microwave scalpel is equipped with a hand switch at one end of an elongated shaft, and the surgeon can use this switch to reenergize the microwave power source during surgery.

In Wappler U.S. Pat. No. 2,002,559, a means for electrosurgically resectioning is disclosed. The device can be used for alleviating organic protrusions obstructing body cavities, and can be utilized for both resectioning and coagulating the tissue by means of suitably generated high frequency electric current. In the course of electrically resectioning a tissue, a channel or groove is cut through the tissue by the development of high frequency, high intensity current at the locus to be resectioned.

In conjunction with the electrode wire used in the resectioning and cauterizing procedure, an endoscope is provided as a part of the instrument for the purpose of completely illuminating the site of the operation. The wire electrode employed for accomplishing the resectioning can be protruded out of the shaft upon which it is mounted, so as to form a section which will engage broadside against the tissue which is to be cut. The technique further involves the use of a grounding or indifferent electrode which is made to contact the patient at some suitable point on the body. The patentee states that the type of current employed renders the cutting operation using this device entirely hemostatic, and accomplishes the resectioning in a rapid, simple manner which requires only local anesthesia.

In U.S. Pat. No. 4,506,668, a resectoscope is depicted and described which includes a high frequency cutting loop. The loop is generally U-shaped or semicircular in configuration and is mounted at the end of an extended or elongated tubular shaft. As with other high frequency cutting loops, the grounding of the patient is utilized to constitute the other terminal of the electrical circuit. The flow of current at some distance from the loop is at a harmlessly low level, but in the intermediate vicinity of the loop, the current density is highly concentrated and therefore creates a considerable rise in temperature. In this way, the loop acts to cut tissue.

Other types of electrosurgical instruments utilized for severing or cutting through tissues of the body are shown in Doane U.S. Pat. No. 1,919,543, Morrison U.S. Pat. No. 3,801,766 and Nottke U.S. Pat. No. 4,427,006. Both of the latter patents disclose electrosurgical devices having a control switch means in the instrument handle area.

The physical principles involved in electrosurgically resectioning tissues and concurrently accomplishing coagulation or cauterization are generally well understood, and have been incorporated in several different types of electrosurgical instruments. These are typified by those disclosed in the patents which have been referenced. New applications of these types of electrosurgical techniques other than those which are described in these patents await the address of persons working in this technology. One particular need has been perceived by the present inventors to reside in the field of veterinary medicine, and particularly, in the case of equine surgery employed to alleviate blockage of the air passageway and windpipe of a horse. This blockage occasionally results from an abnormal displacement of the soft palate from its normal position, in which it extends under the epiglottis and immediately above the oropharnynx, to a position in which it extends across and above the epiglottis. In the latter position, the soft palate extends across and occludes a portion of the air passageway extending the mouth and nasal passageways via the larynx to the trachea and windpipe. When this condition occurs, the animal has difficulty in breathing, and particularly when racing or running extended distances. In the latter cases, larger volumetric air intake is required in order to supply the greatly enhanced oxygen demands of the body.

BRIEF DESCRIPTION OF THE PRESENT INVENTION

The present invention provides both an apparatus and a technique by which a displaced soft palate of an equine animal can be electrosurgically resectioned so as to centrally severe the palate, and make it possible for the palate to recede to its normal position beneath the epiglottis. The air passageway is thus cleared, and the partial obstruction or occlusion which has previously been caused by the displacement of the palate is alleviated.

Broadly described, the electrosurgical resectioning and cauterizing instrument of the present invention includes an elongated shaft having a length of between about 24 and 40 inches. The shaft is constructed so as to be semirigid and capable of retaining a particular shape while in use, yet it can be forceably caused to undergo flexure for negotiating turns, or changes of direction, within an equine nasal passageway. This allows the instrument to be moved to its effective operating position. The elongated shaft or rod supports an electrical conductor extended over its length and secured to the shaft by a plastic sheath or sleeve which is heat shrunk onto the rod for purposes of retaining the conductor in position. The heat shrunk plastic is an electrically non-conductive material. At its distal end, the shaft carries a bight, and at this location the conductor, which has been extended to the end of the shaft, has a cutting section in the form of a wire extended from the end of the shaft across the bight in an exposed, cutting position.

At its other end, the elongated shaft is connected to a pistol-grip switch handle. A three-position toggle switch is mounted in the handle and is connected in an electrical circuit which includes the conductor, and also a grounding lead which leads to a grounding plate. The toggle switch can be pivoted to a coagulating mode position or to a cutting mode position by a surgeon holding the pistol-grip handle.

In practicing the surgical method using the described apparatus, the surgeon initially inserts the bight-carrying end of the shaft into one of the nasal passageways of an afflicted equine animal which is suffering from reduction of breathing inhalation capacity as a result of a partial occlusion of the windpipe by abnormal displacement of the soft palate in the manner hereinbefore described. Concurrently, an illuminating endoscope is inserted in the other nasal passageway and interiorly functions, when advanced to the right location, to illuminate the bight-carrying end of the electrosurgical instrument. At this point, both the shaft and the endoscope have been advanced into the respective nasal passageways until illumination of the bight by the endoscope shows it to be positioned immediately over the center of the displaced soft palate.

The pistol-grip handle is then grasped and manipulated to bring the section of the conductor which crosses the bight of the shaft into contact with the center of the soft palate. The conductor is then placed in a cutting status by using the finger to move the switch to the cutting mode position. The handle is then used to retract the shaft slowly in a direction to withdraw it from the nasal passageway. This retractive motion in turn causes the conductive wire crossing the bight portion of the shaft to cut into, and through, the soft palate, cleaving it in along a longitudinal centerline so that the palate can be more easily retracted by the animal into the proper normal position beneath the epiglottis. The occlusion of the air passageway is thus relieved.

An important object of the present invention is to provide an improved electrosurgical resectioning instrument which is especially adapted for use in an equine surgical technique by which an abnormally displaced soft palate can, by surgical resectioning of the soft palate, be prevented from blocking or partially occluding the windpipe and air passageways of an equine animal.

A further object of the invention is to provide a relatively inexpensive, but highly useful and reliable electrosurgical instrument which can be used for surgically cutting through the soft palate of an equine animal in a way which permits the soft palate to be displaced to a more acceptable, and more natural, position in the air passageway system of the equine animal.

A further object of the invention is to provide an electrosurgical instrument useful by veterinarians for performing surgical cutting procedures at a location which is instrumentally accessible through the nasal passageways of large equine animals.

Additional objects and advantages of the invention will become apparent as the following detailed description of the invention is read in conjunction with the accompanying drawings which illustrate a preferred embodiment of the invention.

GENERAL DESCRIPTION OF THE DRAWINGS

FIG. 1 is a side elevation view of the equine electrosurgical instrument of the invention.

FIG. 2 is a section view taken along line 2—2 of FIG. 1.

FIG. 3 is an enlarged, detailed view of the tip of the electrosurgical instrument at which the cutting span of the electrical conductor is located.

FIG. 4 is a diagrammatic illustration of a horse's head, illustrating the nasal passageway at one side of the head, the soft palate, the epiglottis and the trachea, all in order to facilitate the description of the use of the electrosurgical instrument, and of the method or surgical technique of the present invention.

DETAILED DESCRIPTION OF A PREFERRED EMBODIMENT OF THE INVENTION

Referring initially to FIG. 1 of the drawings, the equine electrosurgical instrument of the invention includes an elongated shaft or rod 10 which is preferably of generally circular cross-section as shown in FIG. 2. The shaft or rod 10 preferably defines a very large, flat angle of from about 165° to about 175° located about two-thirds of the way along its length as shown at 11 in FIG. 1. The shaft 10 can be constructed of stainless steel or copper. Other materials can also be used, provided they have sufficient rigidity to remain configured generally as shown in FIG. 1, yet can undergo flexing sufficiently to permit it to be pushed through the nasal passageway of a horse. In accomplishing this, slight bending of the shaft will often be required in order to reach the location of the soft palate and epiglottis at the upper end of the air passageway or windpipe. The shaft or rod 10 is preferably from about three-sixteenths inch to about three-eighths inch in diameter, with about one-fourth inch being preferred.

Extended along the bottom side of the shaft or rod 10 is an electrical conductor 12 which is preferably sixteen gauge, multiple stranded, nickel-coated copper wire. The conductor 12 extends over a major portion of the length of the rod 10. The conductor 12 is held to the underside of the rod 10 by means of a heat-shrink plastic sheath which is shrunk upon the rod to form an elongated tubing 14 extending from one end of the rod to the other, as depicted in FIGS. 1 and 2. Preferably, the heat shrinkable plastic material employed is polyvinylchloride (PVC).

The shaft or rod 10 and its tubing or sleeve 14 of heat shrunk plastic may be described as having a distal end and a proximal end. At the distal end portion of the rod 10, the rod is bent through a substantially semicircular configuration to form an arcuate bight portion 16. As shown in FIG. 3, the bight portion 16 located at the distal end of the rod 10 has been exposed (for clarity of illustration and description) by removal of a part of the electrically insulating, or non-conductive material, in which it is insheathed as shown at 14. The bight portion 16 will typically have a radius of curvature of from about one-half inch to about one and one-half inches.

It will be noted that at the point where the curvature of the bight portion 16 commences, the stranded copper conductor 12 is bonded to a relatively short length of platinum wire 18 by means of silver solder depicted at 20. The platinum wire 18 is extended across the bight portion 16 to form a straight, exposed cutting section 18a. The exposed cutting section 18a of the platinum wire 18 is between two inches and four inches in length, and preferably is about three inches in length. Further, it preferably extends at an angle which is from about 20° to about 80° with respect to the longitudinal axis of the rod 10 at the location where the platinum wire is extended back to the rod. Preferably the cutting section 18a extends at an angle of about 45° to the longitudinal axis of the rod or shaft 10. It should be pointed out that the tip of the platinum cutting section 18a is insulated from the copper conductor 12 at the location where the platinum cutting section ends.

At the proximal end of the shaft 10, the shaft is fitted into a receiving sleeving subassembly 22 which is itself covered with the heat shrunk PVC material 14 as previously described. The sleeving subassembly 22 is joined to the electrically nonconductive housing of a pistol-grip handle subassembly 24. The pistol-grip handle subassembly includes a grip portion 26, made of an electrically non-conductive material, and a finger-manipulatible toggle switch 28.

The toggle switch 28 is a three-position switch, with the solid line position shown in FIG. 1 being the "off" position. When the toggle switch 28 is pushed upwardly toward the rod 10, it is moved to the "coagulating mode". When it is pushed downwardly, it is thrown into the "cutting mode". The copper conductor 12 extends from the bottom, or free end, of the grip portion 26 of the pistol-grip handle subassembly, and is insulated over its entire length from that point to the point where it is connected to a conventional plug 30.

The diagrammatic illustration of the head of a horse which is set forth in FIG. 4 is provided to facilitate the explanation of the surgical method or technique which is carried out using the equine electrosurgical instrument shown in FIG. 1. The section of the horse's head which is illustrated is a sagital section taken just to the left of the median plane through the head of the horse. The left nasal cavity is illustrated at 32. The soft palate in its normal position is illustrated in solid lines at 34. In this position, the soft palate lies above the tongue of the horse and extends over the tonsil and beneath the epiglottis 36. The epiglottis 36 defines one side of the vestibule of the larynx 37. The larynx then opens into the trachea 38 which, of course, leads to the lungs. Immediately above the epiglottis 36 is the pharynx 40 which connects the larynx to the nasal cavity 32.

In the natural and normal positions of the described organs in the animal, the internal tip portion of the soft palate 34 extends beneath the epiglottis 36 as illustrated in solid lines, and in this fashion, functions, in part, to prevent the escape of any food into the trachea or windpipe 38.

In some animals, however, an unnatural condition can occur in which the soft palate is displaced from the location illustrated in solid lines to a position upwardly therefrom illustrated in dashed lines, in which it lies atop or extends partially across the epiglottis 36 and partially into the larynx vestibule 37. In this position, the soft palate 34 is an obstruction preventing the full and free flow of air from the nasal passageways 32 through the larynx to the trachea 38. The animal thus has greater difficulty breathing, and in the case of race horses, for example, this is particularly undesirable.

In one previously used surgical technique, a sharp hook was extended through the nasal cavity to a location where the soft palate could be engaged by the hook and the surgeon then simply forcibly pulled away the soft palate with a great amount of hemorrhaging and trauma resulting to the animal. Recovery was slow and the risk of post-operative complication was relatively great. In another technique, an incision was made through the neck of the horse to reach the locus of the occlusion, and the palate was then cleft by the use of suitable surgical procedure. Cleaving of the palate generally permitted it to return to the normal position below the epiglottis. In this case also, the time required for recovery from the surgery was more extended than desirable.

In the utilization of the technique of the present invention, employing the equine electrosurgical instrument depicted in FIG. 1, the veterinarian initially anesthetizes the animal for a period of time adequate to permit the procedure to be carried out. Usually, this will not exceed about 45 minutes.

After anesthesia, the veterinarian inserts the distal end of the tool at which the bight portion 16 is located into one of the nasal passageways and slowly works the distal end of the instrument inwardly until it reaches the pharynx. It should be noted at this point that the heat shrinkable, electrically nonconductive plastic material 14 with which the rod or shaft 10 is covered, coupled with the general convex curvature of the bight portion 16, prevents the rod from cutting, abrading, ripping or gouging the tender tissues which line the nasal passageways.

Concurrently with the introduction of the distal end portion of the electrosurgical instrument into the nasal passageway, an endoscope or other suitable illuminating and mirror-carrying device is inserted in the other nasal passageway of the horse, and is advanced on a parallel course into the pharynx. Once the endoscope is in the pharynx, along with the distal end of the electrosurgical instrument, the pistol-grip handle 26 can be grasped and used to manipulate the bight portion 16 of the handle to a position such that the cutting portion 18a of the conductor 12 is made to extend immediately over the center of the soft palate. In this position, the platinum wire cutting portion 18a lies in substantially the same plane as the longitudinal axis of the soft palate. The handle grip 26 is then grasped, and the electrosurgical instrument is retracted until the wire is in immediate proximity to, or in contact with, the soft palate. The veterinarian then moves the toggle switch 28 downwardly to the lower dashed line position illustrated in FIG. 1. In this position, the circuit is closed and the platinum wire conductor 18a is placed in a cutting mode. The soft palate is thus cut through, and is divided into two roughly equal parts on each side of the resection line.

As is understood from the present state of the art, the current which is discharged in high density immediately adjacent the platinum conductor wire 18a is dissipated through the body of the animal and the circuit is completed by reason of a ground plate, or neutral plate, which is placed on the neck of the animal at a location immediately below the place where the mislocated soft palate is positioned within the throat of the animal. After the soft palate has been cut through by continued retraction of the electrosurgical instrument through the nasal passageway of the horse, the instrument is then once again caused to advance slowly inwardly in the nasal passageway so that the platinum wire cutting section 18a is moved along the line where the palate has previously been cut. During this movement, the toggle switch 28 is thrown to the cauterizing mode, which mode is the upper dashed line position illustrated in FIG. 1. In the cauterizing mode, the heat from the high frequency current cauterizes the tissue adjacent the line along which the soft palate has been cut, and thus prevents any significant hemorrhaging from the cut.

After this has been accomplished, the electrosurgical instrument is slowly retracted through the nasal passageway to remove it from the head of the horse. The same retractive recovery is carried out with the endoscope. The horse is then allowed to recover from the anesthesia, and is not subjected to any heavy exercise for several days in order to prevent excessive stress to the air passageways and organs which have been affected by the described surgical technique.

The procedure described is simple, and complications resulting from its use have been rare. In most equine animal cases, the described surgery can be very easily and successfully accomplished.

Although a preferred embodiment of the invention has been herein described, it will be understood that various changes and innovations can be made in the illustrated and described structure without departure from the basic principles upon which the invention is based. Changes and innovations of this type are therefore deemed to be circumscribed by the spirit and scope of the invention except as the same may be necessarily limited by the appended claims, or reasonable equivalents thereof.

What is claimed is:

1. An equine electrosurgical instrument comprising:

an elongated, manually bendable shaft having a proximal end, and having a digital end portion, said shaft further including a bight portion of rounded, semi-circular configuration at, and forming a major part of, the distal end portion of said shaft, said bight portion defining an open mouth;

a handle of electrically non-conductive material secured to the proximal end of said shaft and configured to facilitate axial reciprocation of said shaft and concurrent rotative movement of said bight portion and said handle about the longitudinal axis of said shaft;

elongated electrical conductor means secured to said shaft and extending from the proximal end thereof to said distal end portion, said electrical conductor means including a cutting section extending across said bight portion to block the mouth of the bight portion;

a sleeve of electrically non-conductive material encasing said shaft and a major portion of said conductor means except for said cutting section, and extending from the proximal end to the distal end portion of the shaft, including said bight portion;

switch means on said handle and electrically connected to said conductor means for cutting and for cauterizing flesh in contact with said cutting section; and additional circuit components comprising a plug and electrical leads extending through said handle to said shaft and connecting said plug to said conductor means and to said switch means.

2. An equine electrosurgical instrument as defined in claim 1 wherein said elongated shaft has a length of from about twenty-four inches to about forty inches and has a circular cross-sectional configuration, with a diameter over a major portion of its length of from about three-sixteenths inch to about three-eighths inch, and wherein the bight portion of said shaft is of arcuate, substantially semicircular configuration.

3. An equine electrosurgical instrument as defined in claim 2 wherein said semicircular bight portion has a radius of from about 1 inch to about 1½ inches.

4. An equine electrosurgical instrument as defined in claim 2 wherein said elongated electrical conductor means comprises a plurality of copper conductor wires multi-stranded together and nickel-coated, said wires extending from the proximal end of said shaft toward said distal end portion, said electrical conductor means further including, as said cutting section, a platinum wire connected to said copper wires and extending across the mouth of said bight.

5. An equine electrosurgical instrument as defined in claim 2 wherein said conductor means comprises:
  a copper conductor extending from said proximal end to said bight portion; and
  a platinum wire connected to said copper conductor and extending across said bight to form a cutting section.

6. An equine electrosurgical instrument as defined in claim 2 wherein said sleeve of electrically non-conductive material comprises a coating of heat shrinkable polyvinylchloride.

7. An equine electrosurgical instrument as defined in claim 1 wherein said elongated electrical conductor means comprises a plurality of copper conductor wires multi-stranded together and nickel-coated, said wires extending from the proximal end of said shaft toward said distal end portion, said electrical conductor means further including, as said cutting section, a platinum wire connected to said copper wires and extending across the mouth of said bight.

8. An equine electrosurgical instrument as defined in claim 1 wherein said handle is a pistol-grip handle, and wherein said switch means is mounted on said handle at a location to permit said switch means to be opened and closed by means of one finger while said pistol-grip handle is gripped with the remaining fingers and thumb of one hand.

9. An equine electrosurgical instrument as defined in claim 1 wherein said switch means comprises a three-position toggle switch having one operating position in which a cutting current is delivered to said cutting section of said elongated electrical conductor means, and a second operating position in which a cauterizing current is delivered to said cutting section of said elongated electrical conductor means, and a third position which is an "off" position interrupting the flow of current to said conductor means.

10. An equine electrosurgical instrument as defined in claim 1 wherein said sleeve of electrically non-conductive material comprises a coating of heat shrinkable polyvinylchloride.

11. An equine electrosurgical instrument as defined in claim 1 wherein said conductor means comprises:
  a copper conductor extending from said proximal end to said bight portion; and
  a platinum wire connected to said copper conductor and extending across said bight to form a cutting section.

12. An equine electrosurgical instrument as defined in claim 1 wherein said switch means is a three-position toggle switch mounted on said handle at a location to permit said toggle switch to be shifted by means of one finger while said handle is gripped with the remaining fingers and thumb on the hand on which said one finger is located, said switch having a "cutting" position, a "cauterizing" position and an "off" position.

13. An equine electrosurgical instrument comprising:
  an elongated shaft of a semirigid, manually bendable material capable of sustaining a shape to which it is bent, said shaft having a length of from about 24 inches to about 40 inches, having a proximal end and having a distal end portion, having a cross-section of sufficiently small transverse dimension to pass easily into one of the nostrils of a horse and into the nasal passageway and pharynx of the horse, said shaft further having a rounded bight portion of generally semicircular configuration located at, and forming a major part of, the distal end portion of said shaft, said shaft being bent to form an angulation therein of from about 165° to about 175° at a location which is about two-thirds of the distance from said proximal end to said distal end portion;
  a pistol-grip handle secured to one end of said shaft and constructed to facilitate gripping of the pistol-grip handle without an electrically conductive path being established between the hand of a person gripping the handle and any energized electrical circuit components in said instrument;
  elongated electrical conductor means secured to said shaft and extending along one side thereof from the proximal end of the shaft to said distal end portion, said electrical conductor means including a cutting section extending in a straight line across said bight portion to block the mouth of said bight portion;
  a sleeve of electrically non-conductive material closely encasing and surrounding said shaft over a major portion of the length of said shaft, and over a major portion of said conductor means, but not encasing or covering the cutting section of said conductor means, said sleeve extending from the proximal end of the shaft to the distal end portion of the shaft and encasing the bight portion at the distal end portion of said shaft;
  switch means mounted on said handle in a finger accessible position and connectable in an electrical circuit including said conductor means, said switch means functioning, when closing said circuit, to selectively deliver a cutting current, and alternatively, a cauterizing current, to said cutting section for cutting and cauterizing flesh in contact with said cutting section; and
  an electrical plug electrically connected to said conductor means, and facilitating the connection of said conductor means to a source of electrical current.

14. A method for electrosurgically resectioning the soft palate of a horse which includes:

forming an electrosurgical instrument which includes an elongated shaft carrying an electrical conductor over its length and having a proximal end and a distal end portion, which distal end portion includes:

a semicircular bight portion having a convex, rounded side facing away from the proximal end of said shaft;

inserting the bight-carrying distal end portion of the shaft into one of the nasal passageways of a horse suffering from a reduction in breathing inhalation capability as a result of a partial occlusion of the windpipe by unnatural displacement of the soft palate;

inserting an illuminating endoscope in the other nasal passageway of the horse;

advancing both the shaft of the electrosurgical instrument and the endoscope into the respective nasal passageways until the endoscope shows the semicircular bight portion on the distal end portion of the shaft to be positioned over the displaced soft palate; then manipulating the handle and shaft to bring the exposed wire section of the conductor extending across the open side of the bight portion into contact with the center of the soft palate;

placing the electrosurgical instrument in a cutting status by energization of the electrical conductor after having placed a ground plate topically upon the neck of the horse; and finally drawing the electrosurgical instrument in a direction to retract the bight portion generally toward the opening of the nasal passageway into which the electrosurgical instrument was inserted so as to cut through and cleave the soft palate as the electrically energized conductor is moved through the soft palate.

* * * * *

UNITED STATES PATENT AND TRADEMARK OFFICE
CERTIFICATE OF CORRECTION

PATENT NO. : 4,887,593

DATED : December 19, 1989

INVENTOR(S) : Michael J. Wiley, Helen J. Albrecht & Albie A. Dale

It is certified that error appears in the above-identified patent and that said Letters Patent is hereby corrected as shown below:

In the Claims:

Column 8, line 47 (claim 1), change "digital" to -distal-

Signed and Sealed this

Fourth Day of December, 1990

Attest:

HARRY F. MANBECK, JR.

*Attesting Officer*  *Commissioner of Patents and Trademarks*